United States Patent
Basale et al.

(10) Patent No.: US 7,514,524 B2
(45) Date of Patent: Apr. 7, 2009

(54) METHODS FOR PRODUCING AND PURIFYING 2-HYDROCARBYL-3,3-BIS(4-HYDROXY ARYL)PHTHALIMIDINE MONOMERS AND POLYCARBONATES DERIVED THEREFROM

(75) Inventors: Rajshekhar Basale, Karnataka (IN);
Balakrishnan Ganesan, Karnataka (IN);
Venkata Rama Narayanan Ganapathy Bholta, Bangalore (IN); Gurram Kishan, Karnataka (IN); Surendra Kulkarni, Karnataka (IN); Pradeep Nadkarni, Karnataka (IN); Suresh Shanmugam, Karnataka (IN); Ravindra Vikram Singh, Utter Pradesh (IN)

(73) Assignee: SABIC Innovative Plastics IP B.V., Bergen op Zoom (NL)

( * ) Notice: Subject to any disclaimer, the term of this patent is extended or adjusted under 35 U.S.C. 154(b) by 67 days.

(21) Appl. No.: 11/694,405

(22) Filed: Mar. 30, 2007

(65) Prior Publication Data
US 2008/0242829 A1    Oct. 2, 2008

(51) Int. Cl.
*C08G 64/00* (2006.01)
*C08G 63/02* (2006.01)

(52) U.S. Cl. .................. 528/196; 359/642; 525/58; 525/125; 525/133; 525/176; 525/178; 525/433; 528/198; 528/271; 528/272; 548/471; 548/472

(58) Field of Classification Search .............. 359/642; 525/58, 125, 133, 176, 178, 433; 528/196, 528/198, 271, 272; 548/471, 472
See application file for complete search history.

(56) References Cited

U.S. PATENT DOCUMENTS

| | | | |
|---|---|---|---|
| 1,583,372 A | 5/1926 | Schudel | |
| 1,681,361 A | 8/1928 | Pasternack | |
| 1,940,146 A | 12/1933 | Roberts | |
| 1,940,495 A | 12/1933 | Hubacher | |
| 1,965,842 A | 7/1934 | Kranz | |
| 2,192,485 A | 3/1940 | Hubacher | |
| 2,522,939 A | 9/1950 | Gamrath | |
| 2,522,940 A | 9/1950 | Martin | |
| 4,217,438 A | 8/1980 | Brunelle et al. | |
| 4,252,725 A | 2/1981 | Prindle et al. | |
| 7,135,577 B2 | 11/2006 | Rai et al. | |
| 7,277,230 B2 * | 10/2007 | Srinivasan et al. | 359/642 |
| 2005/0222334 A1 * | 10/2005 | Srinivasan et al. | 525/178 |
| 2005/0228137 A1 * | 10/2005 | Srinivasan et al. | 525/186 |
| 2006/0106234 A1 | 5/2006 | Tran-Guyon et al. | |
| 2007/0010619 A1 | 1/2007 | Chatterjee at el. | |

FOREIGN PATENT DOCUMENTS

EP     1582549     10/2005
WO     2007064630     6/2007

OTHER PUBLICATIONS

International Search Report for International Application No. PCT/US2007/073953, mailed Nov. 22, 2007, 6 pages.
Written Opinion for International Application No. PCT/US2007/073953, mailed Nov. 22, 2007, 6 pages.
Japanese Publication No. 60115662, Published Jun. 22, 1985, Abstract Only, 1 page.
Japanese Publication No. 60127369, Published Jul. 7, 2008, Abstract Only, 1 page.
Fl. Ouiban, St. Oilianu and Sofia Toodorescu. "The Synthesis of Phenolphthalein with Chemistry", vol. 1958 9 p. 151-2, (1958).
Lin, M.S. and E.M. Pearce. "Polymers with Improved Flammability Characteristics. I. Phenolphthalein-Related Homopolymers", Journal of Polymer Science: Polymer Chemistry Editiion, vol. 19, pp. 2659-2670 (1981).
Shuxian, Hu. "Study of the Preparation of Phenolphthalein Using Sulfonic Acid Type Cation Exchange Resin as Catalyst",Ion Exchange and Adsorption/Lizi Jiaohuan Yu Xifu, vol. 5(6), pp. 454-457 (1989).
Vaijula, Raghunadh, "Effect of Cation Exchange Resin in the Preparation of Phenolphthalein", Indian Journal of Technology, vol. 26, Oct. 1988, pp. 491-494.
Cilianu, et al, abstract of Romanian Patent No. 91178, published Mar. 30, 1987.
Fl. Ouiban, et al., abstract of "The synthesis of phenolphthalein with chlorosulfonic acid as the condensation agent", vol. 1958 9 p. 151-2, (1958).

* cited by examiner

Primary Examiner—Terressa M Boykin

(57) ABSTRACT

Disclosed herein is a method comprising reacting a phenolphthalein material and a primary hydrocarbyl amine in the presence of an acid catalyst to form a reaction mixture comprising 2-hydrocarbyl-3,3-bis(4-hydroxyaryl)phthalimidine, wherein the phenolphthalein material comprises greater than or equal to 95 weight percent phenolphthalein, based on the total weight of phenolphthalein material; quenching the reaction mixture and treating the quenched reaction mixture to obtain a first solid. The first solid is then triturated with a trituration solvent and washed to obtain a second solid, wherein the second solid comprises greater than or equal to 97 weight percent 2-hydrocarbyl-3,3-bis(4-hydroxyaryl)phthalimidine, based on the total weight of the second solid. The second solid may be polymerized to form a polycarbonate.

22 Claims, No Drawings

METHODS FOR PRODUCING AND PURIFYING 2-HYDROCARBYL-3,3-BIS(4-HYDROXYARYL) PHTHALIMIDINE MONOMERS AND POLYCARBONATES DERIVED THEREFROM

BACKGROUND

Phenolphthalein derivatives have been used as aromatic dihydroxy compound monomers to prepare polycarbonate resins as well as polyarylate resins. Phenolphthalein derivatives used as monomers can be difficult to make and isolate with sufficient purity for use in polymer synthesis. Currently available methods to make and isolate phenolphthalein derivatives are lengthy and resource intensive. Accordingly, there remains an unmet need for methods of making and isolating phenolphthalein derivatives suitable for use in polymer synthesis.

BRIEF SUMMARY

In one embodiment, a method comprises reacting a phenolphthalein material and a primary hydrocarbyl amine in the presence of an acid catalyst to form a reaction mixture comprising 2-hydrocarbyl-3,3-bis(4-hydroxyaryl)phthalimidine, wherein the phenolphthalein material comprises greater than or equal to 95 weight percent phenolphthalein, based on the total weight of phenolphthalein material; quenching the reaction mixture and treating the quenched reaction mixture to obtain a first solid. The first solid is then triturated with a trituration solvent and washed to obtain a second solid, wherein the second solid comprises greater than or equal to 97 weight percent 2-hydrocarbyl-3,3-bis(4-hydroxyaryl)phthalimidine, based on the total weight of the second solid; and wherein the 2-hydrocarbyl-3,3-bis(4-hydroxyaryl)phthalimidine is of formula (I):

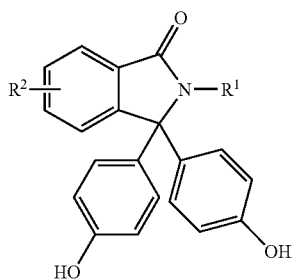

(I)

wherein $R^1$ is selected from the group consisting of a hydrogen and a hydrocarbyl group, and $R^2$ is selected from the group consisting of a hydrogen, a hydrocarbyl group, and a halogen.

In another embodiment, a method of making a polycarbonate comprises reacting a phenolphthalein material and a primary hydrocarbyl amine in the presence of an acid catalyst to form a reaction mixture comprising 2-hydrocarbyl-3,3-bis(4-hydroxyaryl)phthalimidine, wherein the phenolphthalein material comprises greater than or equal to 95 weight percent phenolphthalein, based on the total weight of phenolphthalein material; quenching the reaction mixture and treating the quenched reaction mixture to obtain a first solid. The first solid is then triturated with a trituration solvent and washed to obtain a second solid, wherein the second solid comprises greater than or equal to 97 weight percent 2-hydrocarbyl-3,3-bis(4-hydroxyaryl)phthalimidine, based on the total weight of the second solid; and wherein the 2-hydrocarbyl-3,3-bis(4-hydroxyaryl)phthalimidine is of formula (I); and polymerizing the second solid to form a polycarbonate.

DETAILED DESCRIPTION

This disclosure is directed to producing and purifying phenophthalein derivatives that are suitable for use as monomers for preparing opaque polymers such as opaque polycarbonates as well as preparing opaque polycarbonates from phenolphthalein derivatives. While monomers used to make opaque polymers are not required to have the high level of purity necessary for making clear polymers nonetheless the monomers for opaque polymer synthesis must have sufficient purity to make a stable polymer with desirable properties. It has been discovered that 2-hydrocarbyl-3,3-bis(4-hydroxyaryl)phthalimidine monomer starting materials for polymerization must contain greater than or equal to 97 weight percent, based on the total weight of the 2-hydrocarbyl-3,3-bis(4-hydroxyaryl)phthalimidine monomer starting material, of 2-hydrocarbyl-3,3-bis(4-hydroxyaryl)phthalimidine in order to make a stable polymer. The number of steps required for malting 2-hydrocarbyl-3,3-bis(4-hydroxyaryl) phthalimidine monomer starting materials with the required level of purity has been reduced by the methods described herein, allowing synthesis and isolation with an unexpectedly low yield loss (less than or equal to 10 weight percent). The low yield loss results in a less expensive and more efficient method.

2-hydrocarbyl-3,3-bis(4-hydroxyaryl)phthalimidine is of formula (I):

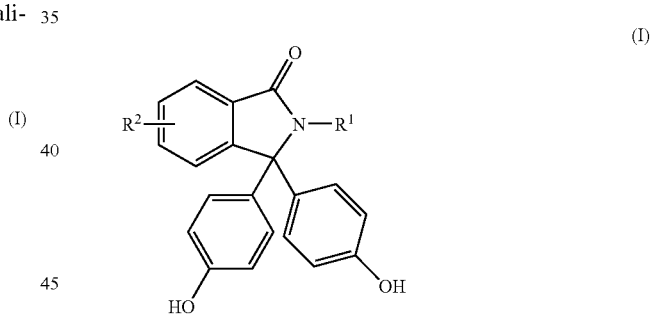

(I)

wherein $R^1$ is selected from the group consisting of a hydrogen and a hydrocarbyl group, and $R^2$ is selected from the group consisting of a hydrogen, a hydrocarbyl group, and a halogen. The 2-hydrocarbyl-3,3-bis(4-hydroxyaryl)phthalimidine can be prepared by the reaction of a phenolphthalein material with a hydrocarbyl amine such as, for example, an aromatic amine (also referred to herein as "aryl amine") of formula (II):

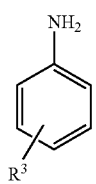

(II)

wherein $R^3$ is selected from a group consisting of a hydrogen, halogen, and a hydrocarbyl group. An exemplary aromatic amine is aniline. The phenolphthalein material comprises greater than or equal to 95 weight percent of a phenolphthalein of formula (III), based on the total weight of the phenolphthalein material:

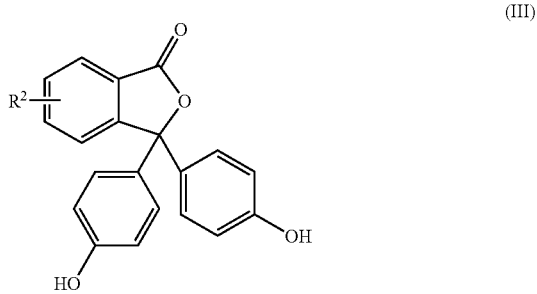

(III)

wherein $R^2$ is as defined above. In one embodiment, the phenolphthalein material comprises greater than or equal to 97, or, more specifically, greater than or equal to 99 weight percent of phenolphthalein, based on the total weight of the phenolphthalein material.

For the purposes of this disclosure, the term "hydrocarbyl" is defined as a monovalent moiety formed by removing a hydrogen atom from a hydrocarbon. Representative hydrocarbyls include, but are not limited to, alkyl groups having 1 to 25 carbon atoms, such as methyl, ethyl, propyl, butyl, pentyl, hexyl, heptyl, octyl, nonyl, undecyl, decyl, dodecyl, octadecyl, nonadecyl, eicosyl, heneicosyl, docosyl, tricosyl, and the isomeric forms thereof; aryl groups having 6 to 25 carbon atoms, such as ring-substituted and ring-unsubstituted forms of phenyl, tolyl, xylyl, naphthyl, biphenyl, tetraphenyl, and the like; aralkyl groups having 7 to 25 carbon atoms, such as ring-substituted and ring-unsubstituted forms of benzyl, phenethyl, phenpropyl, phenbutyl, naphthoctyl, and the like; and cycloalkyl groups, such as cyclopropyl, cyclobutyl, cyclopentyl, cyclohexyl, cycloheptyl, cyclooctyl, and the like. The term "aryl' as used herein refers to various forms of aryl groups that have been described hereinabove for the "hydrocarbyl" group.

An acid catalyst is used to facilitate formation of the phthalimidine product. Suitable acid catalysts include, but are not limited to, mineral acids such as hydrochloric acid (HCl), sulfuric acid, nitric acid, and phosphoric acid; weak inorganic acids such as boric acid, organic sulfonic acids such as methanesulfonic acid, Lewis acids such as stannic chloride, ferric chloride, aluminum trichloride, and zinc dichloride; sulfated zirconia; or combinations of two or more of the foregoing acid catalysts. Suitable acid catalysts also include amine salts of the above mineral acids. Examples of suitable amines include primary, secondary, and tertiary amines having any combination of aliphatic and aromatic groups bonded to the amine nitrogen. Suitable examples of amine salt catalysts include primary, secondary, and tertiary amine hydrochlorides. Hydrochloride salts of the primary aromatic amines of formula (II) are especially useful since the amines of formula (II) also serve as the starting material for preparing the phthalimidines of formula (I).

The catalyst can be introduced as a pre-formed salt into the reactor. Alternatively, the catalyst can be generated in the reactor by first charging an amine of formula (II) into the reactor and then adding 0.1 to 1 part by weight based on the total weight of the amine of an appropriate mineral acid to the reactor. In one embodiment, 0.1 to 0.3 part by weight of hydrogen chloride gas based on the total weight of the amine is introduced into a reactor charged with the amine to form an appropriate amount of the amine hydrochloride catalyst. More hydrochloric acid or more hydrogen chloride gas can also be used, but is generally not required. A solvent can optionally be employed to form the amine hydrochloride. The solvent can then be removed (if necessary), and the amine of formula (II) can be added, followed by addition of phenolphthalein (III).

The reaction of phenolphthalein (III) with the amine (II) proceeds by a condensation reaction to form the desired phthalimidine product (I). An excess of the amine over the phenolphthalein may be used to keep the reaction proceeding in the forward direction. Likewise, a higher reaction temperature with or without water by-product removal can facilitate product formation. However, in order to enhance the selectivity of 2-hydrocarbyl-3,3-bis(4-hydroxyaryl)phthalimidine (I), and suppress the formation of undesired by-product, for example, 2-hydrocarbyl-3,3-{(2-hydroxyaryl)(4-hydroxyaryl)}phthalimidine or 2-hydrocarbyl-3,3-{(4-hydroxyaryl)(4-aminoaryl)}phthalimidine, it is useful to control the temperature of the reaction mixture and the rate of water removal. The temperature of the reaction mixture is controlled such that the crude product is greater than or equal to 97 weight (wt %) percent, or more specifically, greater than or equal to 99 wt% percent, of 2-hydrocarbyl-3,3-bis(4-hydroxyaryl)phthalimidine. The chemical structures of the (2-hydroxyaryl)(4-hydroxyaryl)phthalimidine and (4-hydroxyaryl)(4-aminoaryl)phthalimidine by-products are shown in formulas (IV) and (V), respectively:

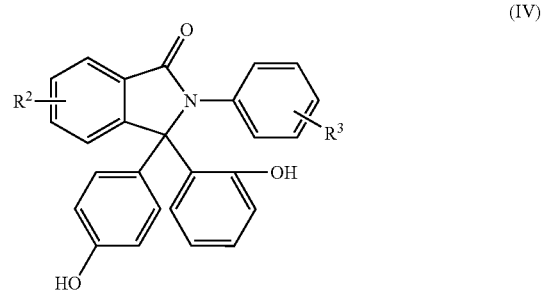

(IV)

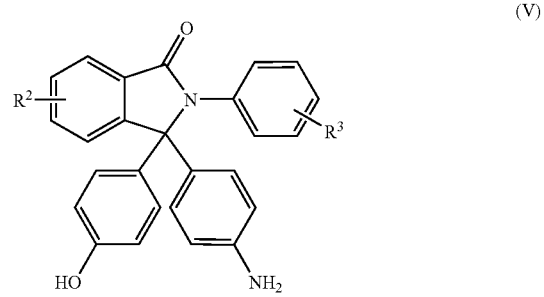

(V)

wherein $R^2$ and $R^3$ are as described above.

In one embodiment, the reaction temperature is controlled such that the water by-product (calculated based on the moles of the phenolphthalein (III) which is used as the limiting reagent) distills over a period of 8 hours to 50 hours, or more specifically, 12 hours to 24 hours. If the reaction mixture is heated such that the amount of water by-product distills within 6 hours, the phthalimidine product of formula (I) can have a relatively greater amount of the (4-hydroxyaryl)(4-aminoaryl)phthalimidine impurity shown in formula (V).

Therefore, although a higher reaction temperature ensures a quicker consumption of the phenolphthalein (III) material, it can lead to formation of a higher amount of the impurity of formula (V) and other impurities can also increase with an increase in temperature and time. If the reaction temperature is not sufficiently high, a relatively large amount of the phenolphthalein material remains unreacted, thereby leading to an inferior product, e.g., forms a less stable polymer during polymerization and subsequent melt mixing, (phenolphthalein can be incorporated into the polycarbonate like 2-hydrocarbyl-3,3-bis(4-hydroxyaryl)phthalimidine) and the like. Thus, in one embodiment, the reaction mixture is heated to a temperature of 140° C. to 180° C. to remove water by-product and form the desired 2-hydrocarbyl-3,3-bis(4-hydroxyaryl) phthalimidine product. In another embodiment, the reaction mixture is heated to a temperature of 152° C. to 157° C. for 12 hours to 24 hours.

By way of example, phenolphthalein ($R^2$ is H in formula (III)) can be reacted with aniline ($R^3$ is H in formula (II)) in the presence of hydrochloric acid as catalyst to form 2-phenyl-3,3-bis(4-hydroxyphenyl)phthalimidine (i.e., para,para-PPPBP or "P,P-PPPBP""), as shown in formula (VI):

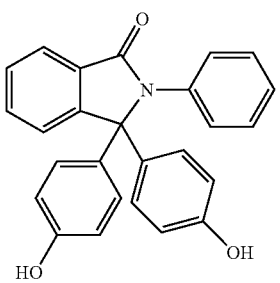

(VI)

Isolation of the desired phenolphthalein derivative from the reaction mixture includes quenching the reaction mixture and treating the quenched mixture to obtain a first solid. The reaction mixture can be quenched with an acid such as an aqueous mineral acid which precipitates a solid comprising 2-hydrocarbyl-3,3-bis(4-hydroxyaryl)phthalimidine and forms a slurry. An exemplary aqueous mineral acid is aqueous hydrochloric acid. Other suitable acids include, but are not limited to, sulfuric acid, boric acid, phosphoric acid, acetic acid, nitric acid, or combinations of two or more of the foregoing mineral acids. The precipitate is isolated from the slurry. Suitable isolation methods include filtration, centrifugation and combinations thereof. The filtration can be conducted either at room temperature (about 25° C.) or at an elevated temperature of 25° C. to 90° C.

The precipitate can be washed with water to obtain a washed precipitate wherein the water has a temperature of 25 to 90° C., or more specifically, 35 to 80° C. The water wash is believed to remove inorganic salts and other water soluble impurities. The amount of water used per wash can be 5 to 15 milliliters (ml) per gram of the precipitate. The water wash step can be repeated several times, for example, 1 to 6 times. In some embodiments the water wash is repeated until the washed precipitate is chloride free as determined by suitable testing such as the silver nitrate test (i.e. chlorides give a white precipitate with silver nitrate—the water wash is tested for the presence of chloride).

Alternatively, the reaction mixture can be quenched with an aqueous base resulting in a biphasic mixture comprising a basic layer. Suitable aqueous bases include sodium hydroxide, potassium hydroxide, sodium carbonate, potassium carbonate and the like. An organic solvent is added to the biphasic mixture. Suitable organic solvents are those solvents in which the primary hydrocarbyl amine has good solubility and has little or no miscibility with the basic layer of the biphasic system. Exemplary solvents include ethylene dichloride, methylene dichloride, chloroform, ethyl acetate, and aromatic hydrocarbons such as toluene, xylene, cumene and benzene. It is also possible to use a mixture of solvents. The basic layer is separated from the biphasic system, optionally treated with an adsorbent such as activated charcoal, and acidified, causing a solid to precipitate. The solid can then be isolated by filtration, centrifugation, or a combination thereof.

After quenching (by either method) the solid is triturated. As used herein, "trituration" is defined as mixing a solid with a trituration solvent and then isolating any undissolved material by filtration, centrifugation or a combination thereof. The trituration solvent is typically chosen such that the desired product has a low solubility in the solvent. During trituration, a portion of the solid such as impurities may dissolve in the solvent. The exact amount of the dissolved material depends on, among other things, the temperature at which the trituration is conducted and the amount of solvent used. Trituration facilitates the removal of any unreacted phenolphthalein. In some embodiments the amount of phenolphthalein in the isolated 2-hydrocarbyl-3,3-bis(4-hydroxyaryl)phthalimidine after trituration is less than or equal to 1,000, or, more specifically, less than or equal to 500 parts by weight per million parts by weight of 2-hydrocarbyl-3,3-bis(4-hydroxyaryl)phthalimidine.

Trituration can be conducted at a temperature above the freezing point of the trituration solvent and less than or equal to the boiling point of the trituration solvent. For example, trituration can be conducted at a temperature of 5 to 70° C. The time required for trituration varies depending on the trituration system and conditions and can be 5 minutes to 4 hours.

Suitable triturating solvents include, but are not limited to, polar solvents, non-polar solvents, and combinations of two or more of the foregoing solvents. Exemplary polar solvents include, but are not limited to, methanol, ethanol, isopropanol, propanol, chloroform, acetone, ethyl acetate, phenol, water, and combinations of two or more of the foregoing.

Exemplary non-polar solvents include, but are not limited to, aromatic hydrocarbons having 6 to 14 carbons, aliphatic hydrocarbons having 5 to 8 carbons, non-polar chlorinated hydrocarbons, and combinations of two or more of the foregoing. Non-limiting examples of suitable aromatic hydrocarbon solvents include toluene, xylene, cumene, benzene and the like. Non-limiting examples of suitable aliphatic hydrocarbon solvents include hexane, cyclohexane, pentane, and the like. Non-limiting examples of non-polar chlorinated hydrocarbon solvents include 1,2-dichloroethane and the like.

Non-limiting examples of suitable triturating solvents comprising mixtures include methanol:toluene, methanol:water, ethyl acetate:toluene, ethyl acetate: 1,2-dichloroethane, acetone: 1,2-dichloroethane, acetone:toluene, acetone:hexane, isopropanol:toluene, acetone:water, and isopropanol:water. The volume ratios (v:v) of the solvent mixtures can be 1:99 to 99:1. Exemplary solvent mixtures include, but are not limited to, methanol:toluene (2:98, v:v), methanol:toluene (13:87, v:v), and methanol:water (90:10, v:v).

After trituration the solid is washed to further remove impurities. Suitable solvents for washing include, but are not limited to, water, methanol, ethanol, isopropanol, propanol, acetone and combinations of two or more of the foregoing solvents. In one embodiment, the washing solvent is methanol:water (90:10, v:v). In another embodiment, the washing solvent is water. In some embodiments the washing solvent is the same as the trituration solvent.

The solid comprises greater than or equal to 97 weight percent 2-hydrocarbyl-3,3-bis(4-hydroxyaryl)phthalimidine of formula (I), based on the total weight of the solid, respectively. In some embodiments, the solid comprises greater than or equal to 99 weight percent 2-hydrocarbyl-3,3-bis(4-hydroxyaryl)phthalimidine.

In one embodiment, the solid can comprise less than or equal to 50 parts per million (or "ppm") by weight of residual solvent based on the total weight of the solid. In some embodiments, the solid comprises less than or equal to 1,000, or more specifically, 500 parts per million by weight of phenolphthalein based on the total weight of the solid.

In one embodiment, the 2-hydrocarbyl-3,3-bis(4-hydroxyaryl)phthalimidine comprises less than or equal to 20,000 parts by weight of a 2-hydrocarbyl-3-{(4-hydroxyaryl)(4-aminoaryl)}phthalimidine impurity per million parts by weight of 2-hydrocarbyl-3,3-bis(4-hydroxyaryl)phthalimidine.

In one embodiment, the solid comprising 2-hydrocarbyl-3,3-bis(4-hydroxyaryl)phthalimidine obtained as described above is polymerizable.

The 2-hydrocarbyl-3,3-bis(4-hydroxyaryl)phthalimidine materials obtained above, including the exemplary 2-phenyl-3,3-bis(4-hydroxyphenyl)phthalimidine, are commercially valuable monomers or comonomers for producing a variety of polymers and polymer compositions formed by reaction of the phenolic OH groups of the 2-hydrocarbyl-3,3-bis(4-hydroxyaryl)phthalimidines. Suitable polymers that can be produced are homopolymers and copolymers of a polycarbonate, a polyestercarbonate, a polyester, a polyesteramide, a polyimide, a polyetherimide, a polyamideimide, a polyether, a polyethersulfone, a polycarbonate-polyorganosiloxane block copolymer, a copolymer comprising aromatic ester, estercarbonate, and carbonate repeat units; and a polyetherketone. A suitable example of a copolymer comprising aromatic ester, estercarbonate, and carbonate repeat units is the copolymer produced by the reaction of a hydroxy-terminated polyester, such as the product of reaction of isophthaloyl chloride, and terephthaloyl chloride with resorcinol, with phosgene and an aromatic dihydroxy compound, such as bisphenol A.

In one embodiment, the polymer produced is a polycarbonate comprising repeating structural units of formula (VIII):

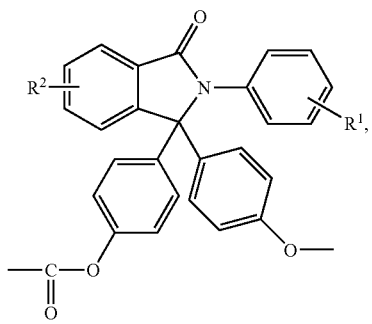

(VIII)

which are derived from 2-hydrocarbyl-3,3-bis(4-hydroxyaryl)phthalimidine. The C=O structural units are derived from a C=O donor such as phosgene or a carbonic acid diester.

The polycarbonate may further comprise structural units derived from at least one other aromatic dihydroxy compound such as those represented by the general formula (IX):

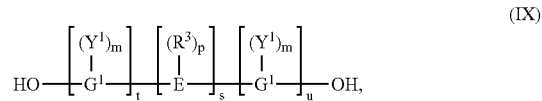

(IX)

wherein each $G^1$ is an independently aromatic group; E is selected from the group consisting of an alkylene group, an alkylidene group, a cycloaliphatic group, a sulfur-containing linkage group, a phosphorus-containing linkage group, an ether linkage group, a carbonyl group, a tertiary nitrogen group, and a silicon-containing linkage group; $R^3$ is a hydrogen, halogen, or a hydrocarbyl group; $Y^1$ is independently selected from the groups consisting of a monovalent hydrocarbyl group, an alkenyl group, an allyl group, a halogen, an oxy group and a nitro group; each m is independently a whole number from zero through the number of positions on each respective $G^1$ available for substitution; p is a whole number from zero through the number of positions on E available for substitution; t is a natural number greater than or equal to one; s is either zero or one; and u is a whole number.

Suitable examples of E include cyclopentylidene, cyclohexylidene, 3,3,5-trimethylcyclohexylidene, methylcyclohexylidene, 2-[2.2.1]-bicycloheptylidene, neopentylidene, cyclopentadecylidene, cyclododecylidene, and adamantylidene; a sulfur-containing linkage such as sulfide, sulfoxide or sulfone, a phosphorus-containing linkage such as phosphinyl, phosphonyl, an ether linkage, a carbonyl group, a tertiary nitrogen group, and a silicon-containing linkage such as a silane or siloxy linkage.

In the aromatic dihydroxy comonomer compound shown in Formula (IX), when more than one $Y^1$ substituent is present, they may be the same or different. The same holds true for the $R^3$ substituent. Where "s" is zero in formula (IX) and "u" is not zero, the aromatic rings are directly joined with no intervening alkylidene or other bridge. The positions of the hydroxyl groups and $Y^1$ on the aromatic nuclear residues $G^1$ can be varied in the ortho, meta, or para positions and the groupings can be in vicinal, asymmetrical or symmetrical relationship, where two or more ring carbon atoms of the hydrocarbon residue are substituted with $Y^1$ and hydroxyl groups. In some embodiments, the parameters "t", "s", and "u" are each one; both $G^1$ radicals are unsubstituted phenylene radicals; and E is an alkylidene group such as isopropylidene. In particular embodiments, both $G^1$ radicals are p-phenylene, although both may be ortho- or meta-phenylene or one ortho- or meta-phenylene and the other para-phenylene.

Some illustrative, non-limiting examples of aromatic dihydroxy compounds of formula (IX) include the dihydroxy-substituted aromatic hydrocarbons disclosed by name or formula (generic or specific) in U.S. Pat. No. 4,217,438. Some particular examples of aromatic dihydroxy compound comonomers include, but are not limited to, bisphenol A; resorcinol; $C_{1-3}$ alkyl-substituted resorcinols; 2,6-dihydroxy naphthalene; hydroquinone; 3-(4-hydroxyphenyl)-1,1,3-trimethylindan-5-ol; 1-(4-hydroxyphenyl)-1,3,3-trimethylindan-5-ol; 4,4'-dihydroxy-diphenyl; 1,1-bis(4'-hydroxy-3'methylphenyl) cyclohexane (DMBPC), 1,1-bis(3,5-dimethyl-4-hydroxyphenyl)cyclohexane; 4,4'-dihydroxydiphenylsulfone (BPS); bis(4-hydroxyphenyl) methane; and 2,2,2',2'-tetrahydro-3,3,3',3'-tetramethyl-1,1'-spirobi[1H-indene]-6,6'-diol. The most typical aromatic dihydroxy compound is Bisphenol A.

In some embodiments, an isosorbide comonomer can be used with the 2-hydrocarbyl-3,3-bis(4-hydroxyaryl)phthalimidine monomer to produce polycarbonate copolymers. Isosorbide, sometimes also called 1,4:3,6-dianhydo-D-glucitol, is a rigid, chemically, and thermally stable aliphatic diol that tends to produce copolymers having higher glass transition temperatures, as compared to comonomer compositions which do not include isosorbide.

The carbonic acid diester described above has the general formula (X):

$$(ZO)_2C=O \quad (X),$$

wherein each Z is independently an unsubstituted or substituted alkyl radical, or an unsubstituted or substituted aryl radical. Suitable examples of carbonic acid diesters include, but are not limited to, ditolyl carbonate, m-cresyl carbonate, dinaphthyl carbonate, diphenyl carbonate, diethyl carbonate, dimethyl carbonate, dibutyl carbonate, dicyclohexyl carbonate, and combinations of two or more carbonic acid diesters thereof. Diphenyl carbonate is widely used as a carbonic acid diester due to its low cost and ready availability on a commercial scale. If two or more of the carbonic acid diesters listed above are utilized, one of the carbonic acid diesters can be diphenyl carbonate.

Suitable carbonic acid diesters also include the group of "activated aromatic carbonates". As used herein, the term "activated aromatic carbonate" is defined as a diaryl carbonate that is more reactive than diphenyl carbonate in a transesterification reaction. Such activated aromatic carbonates can also be represented by formula (X), wherein each Z is an aryl radical having 6 to 30 carbon atoms. More specifically, the activated carbonates have the general formula (XI):

wherein Q and Q' are each independently an ortho-positioned activating group; A and A' are each independently aromatic rings which can be the same or different depending on the number and location of their substituent groups, and a and a' is zero to a whole number up to a maximum equivalent to the number of replaceable hydrogen groups substituted on the aromatic rings A and A' respectively, provided a +a' is greater than or equal to 1. R and R' are each independently substituent groups such as alkyl, substituted alkyl, cycloalcyl, alkoxy, aryl, allcylaryl, cyano, nitro, or halogen. The term b is zero to a whole number up to a maximum equivalent to the number of replaceable hydrogen atoms on the aromatic ring A minus the number a, and the number b' is zero to a whole number up to a maximum equivalent to the number of replaceable hydrogen atoms on the aromatic ring A' minus the number a'. The number, type and location of R or R' on the aromatic ring is not intended to be limited unless they deactivate the carbonate and lead to a carbonate that is less reactive than diphenyl carbonate.

Non-limiting examples of suitable ortho-positioned activating groups Q and Q' include (alkoxycarbonyl)aryl groups, halogens, nitro groups, amide groups, sulfone groups, sulfoxide groups, or imine groups with structures indicated below:

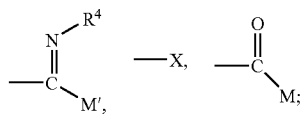

wherein X is halogen or $NO_2$; M and M' independently comprises N-dialkyl, N-alkyl aryl, alkyl, or aryl; and $R^4$ is alkyl or aryl.

Specific non-limiting examples of activated aromatic carbonates include bis(o-methoxycarbonylphenyl)carbonate, bis(o-chlorophenyl)carbonate, bis(o-nitrophenyl)carbonate, bis(o-acetylphenyl)carbonate, bis(o-phenylketonephenyl) carbonate, bis(o-formylphenyl)carbonate. Unsymmetrical combinations of these structures, wherein the substitution number and type on A and A' are different, are also contemplated. An exemplary structure for the activated aromatic carbonate is an ester-substituted diaryl carbonate having the formula (XII):

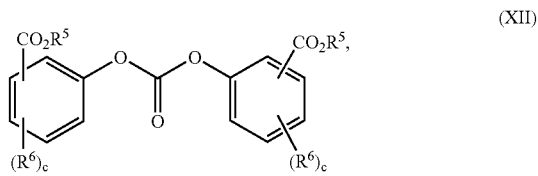

wherein $R^5$ is independently at each occurrence a $C_1$-$C_{20}$ alkyl radical, $C_4$-$C_{20}$ cycloalkyl radical, or $C_4$-$C_{20}$ aromatic radical; $R^6$ is independently at each occurrence a halogen atom, cyano group, nitro group, $C_1$-$C_{20}$ alkyl radical, $C_4$-$C_{20}$ cycloalkyl radical, $C_4$-$C_{20}$ aromatic radical, $C_1$-$C_{20}$ alkoxy radical, $C_4$-$C_{20}$ cycloalkoxy radical, $C_4$-$C_{20}$ aryloxy radical, $C_1$-$C_{20}$ alkylthio radical, $C_4$-$C_{20}$ cycloalkylthio radical, $C_4$-$C_{20}$ arylthio radical, $C_1$-$C_{20}$ alkylsulfinyl radical, $C_4$-$C_{20}$ cycloalkylsulfinyl radical, $C_4$-$C_{20}$ arylsulfinyl radical, $C_1$-$C_{20}$ alkylsulfonyl radical, $C_4$-$C_{20}$ cycloalkylsulfonyl radical, $C_4$-$C_{20}$ arylsulfonyl radical, $C_1$-$C_{20}$ alkoxycarbonyl radical, $C_4$-$C_{20}$ cycloalkoxycarbonyl radical, $C_4$-$C_{20}$ aryloxycarbonyl radical, $C_2$-$C_{60}$ alkylamino radical, $C_6$-$C_{60}$ cycloalkylamino radical, $C_5$-$C_{60}$ arylamino radical, $C_1$-$C_{40}$ alkylaminocarbonyl radical, $C_4$-$C_{40}$ cycloalkylaminocarbonyl radical, $C_4$-$C_{40}$ arylaminocarbonyl radical, or $C_1$-$C_{20}$ acylamino radical; and c is independently at each occurrence an integer 0-4. At least one of the substituents $CO_2R^5$ can be attached in the ortho position of formula (XII).

Examples of ester-substituted diaryl carbonates include, but are not limited to, bis(methylsalkyl)carbonate (CAS Registry No. 82091-12-1) (also known as BMSC or bis(o-methoxycarbonylphenyl)carbonate), bis(ethyl salicyl)carbonate, bis(propyl salicyl) carbonate, bis(butylsalicyl) carbonate, bis(benzyl salicyl)carbonate, bis(methyl 4-chlorosalicyl)carbonate and the like. In one embodiment, BMSC is used in melt polycarbonate synthesis due to its reactivity and its lower molecular weight and higher vapor pressure.

The polycarbonates can comprise structural units indicative of the activated carbonate. These structural units may be end groups produced when activated carbonate fragments act as end capping agents or may be kinlcs introduced into the copolymer by incorporation of activated carbonate fragments.

A number of polymerization methods can be used for producing the polycarbonates. Suitable methods include, but are not limited to, a melt transesterification polymerization method, an interfacial polymerization method, and a bischlorofolmate polymerization method. Detailed polymerization methods are disclosed in U.S. Pat. No. 7,135,577, the entire contents of which are herein incorporated by reference.

In one embodiment, the melt transesterification polymerization method is carried out by combining a catalyst and a reactant composition to form a reaction mixture; and mixing the reaction mixture under reactive conditions for a time period effective to produce a polycarbonate product, wherein the reactant composition comprises a carbonic acid diester and the 2-hydrocarbyl-3,3-bis(4-hydroxyaryl)phthalimidine, wherein the 2-hydrocarbyl-3,3-bis(4-hydroxyaryl)phthalimidine comprises less than or equal to 100 parts per million of a solvent based on the total weight of the 2-hydrocarbyl-3,3-bis(4-hydroxyaryl)phthalimidine. In another embodiment, the 2-hydrocarbyl-3,3-bis(4-hydroxyaryl)phthalimidine comprises less than or equal to 1,000 parts per million of phenolphthalein based on the total weight of the 2-hydrocarbyl-3,3-bis(4-hydroxyaryl)phthalimidine.

During the manufacture of the polycarbonates by the melt transesterification method using the activated or unactivated carbonic acid diester, the amount of the carbonic acid diester comprises 0.8 to 1.3 moles, or more specifically, 0.9 to 1.2 moles, based on one mole of the 2-hydrocarbyl-3,3-bis(4-hydroxyaryl)phthalimidine or any combination of the 2-hydrocarbyl-3,3-bis(4-hydroxyaryl)phthalimidine and at least one aromatic dihydroxy comonomer.

Suitable melt transesterification catalysts include alkali metal compounds, alkaline earth metal compounds, tetraorganoammonium compounds, tetraorganophosphonium compounds, and combinations of two or more of the foregoing catalysts.

The process disclosed herein can be used to prepare 2-hydrocarbyl-3,3-bis(4-hydroxyaryl)phthalimidine homopolycarbonate and copolycarbonates having a weight average molecular weight (Mw) of 3,000 to 150,000 and a glass transition temperature (Tg) of 80 to 300° C. The number average molecular weights (Mn) of the homopolycarbonate and copolycarbonates are from 1,500 to 75,000.

In the interfacial polymerization method, 2-hydrocarbyl-3,3-bis(4-hydroxyaryl)phthalimidine, with or without one or more comonomers, and phosgene are reacted in the presence of a tertiary amine (such as a trialkylamine) and an aqueous base to produce said polycarbonate. An exemplary trialkylamine is triethylamine. Suitable aqueous bases include, for example, the alkali metal hydroxides, such as sodium hydroxide. The interfacial method can be used for producing polycarbonates comprising structural units derived from 2-hydrocarbyl-3,3-bis(4-hydroxyaryl)phthalimidine, and having molecular weights greater than about 50,000, relative to polystyrene standard.

The interfacial method described above can be suitably adapted to produce polycarbonates through the intermediate formation of 2-hydrocarbyl-3,3-bis(4-hydroxyaryl)phthalimidine bischloroformate. This method is sometimes called the bischloroformate polymerization method. In one embodiment, the method comprises reacting a 2-hydrocarbyl-3,3-bis(4-hydroxyaryl)phthalimidine with phosgene in an organic solvent, and then reacting the bischloroformate either with a 2-hydrocarbyl-3,3-bis(4-hydroxyaryl)phthalimidine, or an aromatic dihydroxy compound in the presence of an acid acceptor and an aqueous base to form the polycarbonate.

The interfacial polymerization method and the bischloroformate polymerization method can be carried out in a batch or a continuous mode using one or more reactor systems. To carry out the process in a continuous mode, one or more continuous reactors, such as for example, a tubular reactor can be used. In one embodiment, the continuous method comprises introducing into a tubular reactor system phosgene, at least one solvent (example, methylene chloride), at least one bisphenol, aqueous base, and optionally one or more catalysts (example, a trialkylamine) to form a flowing reaction mixture. The flowing mixture is then passed through the tubular reactor system until substantially all of the phosgene has been consumed. The resulting mixture is next treated with a mixture comprising an aqueous base, at least one end-capping agent, optionally one or more solvents, and at least one catalyst. The end-capped polycarbonate thus formed is continuously removed from the tubular reactor system. The process can be used for preparing end-capped polycarbonate oligomers (generally polycarbonates having a weight average molecular weight of less than or equal to 10,000 daltons) or polymers having a weight average molecular weight of greater than 10,000 daltons. The processes outlined hereinabove can also be suitably adapted, for example, to produce end-capped polycarbonates via the intermediate formation of a mixture comprising a bisphenol monochloroformate or a bisphenol bischloroformate.

Methods for producing and purifying 2-hydrocarbyl-3,3-bis(4-hydroxyaryl)phthalimidine monomers and polycarbonates derived therefrom are further disclosed in the following non-limiting examples.

EXAMPLES

High pressure liquid chromatographic (HPLC) analysis was generally carried out by using a solution of about 50 milligrams of the sample dissolved in about 10 milliliters of methanol. The HPLC instrument was equipped with a $C_{18}$ (reverse phase) column maintained at a temperature of 40° C., and an ultraviolet detector capable of detecting components at a wavelength of 230 nanometers. A solvent mixture of acetonitrile, methanol and water (containing 0.02% phosphoric acid) of gradient elution was used. The flow rate was maintained at 1 milliliter per minute. Assay was computed by calculating the phenolphthalein content using suitable calibration for phenolphthalein and the weight percent of all other impurities was calculated using the response factor of PPPBP. The purity of PPPBP was calculated by subtracting the amount of phenolphthalein and "others" from 100.

Examples 1 to 3 and Comparative Example A

The phenolphthalein starting material (50 grams) had a purity of 99.27%. The molar ratio of aniline:phenolphthalein:HCl in the reaction mixture was 3:1:1. The reactions were quenched with 375 milliliters (ml) of 4 wt % aqueous NaOH to form a biphasic system. 1,2-dichloroethane was added to the biphasic system and the basic layer was separated. The basic layer was mixed with activated carbon (5 weight % based on the theoretical weight of 2-hydrocarbyl-3,3-bis(4-hydroxyphenyl)phthalimidine) and filtered. Aqueous HCl (10 wt %) was added and a precipitate formed which was isolated by filtration. The precipitate contained 2-hydrocarbyl-3,3-bis(4-hydroxyphenl)phthalimidine and impurities. Data is shown in Table 1.

TABLE 1

| | Reaction Temp. (°C.) | Reaction Time (hours) | 2-hydrocarbyl-3,3-bis(4-hydroxyphenyl)phthalimidine wt % | Phenolphthalein Impurity in Product, % | A,P-PPPBP Impurity in Product % | Total other Impurities % | Product Yield % |
|---|---|---|---|---|---|---|---|
| 1 | 170-171 | 13 | 97.9 | 0.46 | 1.10 | 0.48 | 94 |
| 2 | 165-167 | 20 | 98.5 | 0.33 | 0.75 | 0.41 | 94 |
| 3 | 155-157 | 24 | 98.4 | 0.91 | 0.34 | 0.35 | 94 |
| A | 150-151 | 24 | 96.5 | 2.96 | 0.13 | 0.41 | 91 |

The precipitate comprising 2-hydrocarbyl-3,3-bis(4-hydroxyaryl)phthalimidine was further purified using trituration and washing. Ten grams of each precipitate was used for purification. The samples were triturated with 40 ml of methanol:water (90:10, v:v) and washed with 10 ml of methanol:water (90:10, v:v). Trituration was conducted at 70° C. for 30-120 minutes. After the methanol:water wash the solid was washed with 20 ml of water. The results are summarized in Table 2.

TABLE 2

| Ex. # | Phenolphthalein impurity, % | A,P-PPPBP impurity, % | Total other impurities, % | Yield loss | 2-hydrocarbyl-3,3-bis(4-hydroxyphenyl)phthalimidine, wt % |
|---|---|---|---|---|---|
| 1 | 0.03 | 1.09 | 0.2 | 7% | 98.70% |
| 2 | 0.01 | 0.70 | 0.2 | 7% | 99.09% |
| 3 | 0.04 | 0.33 | 0.1 | 7% | 99.50% |

As can be seen from the data in Table 2, trituration and wash of the 2-hydrocarbyl-3,3-bis(4-hydroxyphenyl)phthalimidine products improved their purity while having only minimal yield loss (about 7 wt %).

Examples 4 to 11

In Examples 4 to 11, 100 grams of crude phenolphthalein starting materials having a purity of 95 wt % were used to prepare 2-hydrocarbyl-3,3-bis(4-hydroxyaryl)phthalimidine products. The molar ratio of aniline:phenolphthalein:HCl in the reaction mixture was 3:1:1. The reaction conditions are shown in Table 3. The reactions were quenched with 4 wt % aqueous NaOH. 1,2-dichloroethane was added to the biphasic system and the basic layer was separated. The basic layer was mixed with activated carbon (5 weight % based on the theoretical weight of 2-hydrocarbyl-3,3-bis(4-hydroxyphenyl)phthalimidine) and filtered. Aqueous HCl was added (10 wt %) and a precipitate formed which was isolated by filtration. The precipitate contained crude 2-hydrocarbyl-3,3-bis(4-hydroxyphenyl)phthalimidine and impurities. Results are shown in Table 3.

TABLE 3

| | Time (hour) | Temp (°C.) | Output (g) | AP impurity (%) | PP impurity (%) | Total other impurity, % | Product purity (%) |
|---|---|---|---|---|---|---|---|
| 4 | 25 | 152-154 | 85 | 0.93 | 0.92 | 4.43 | 93.72 |
| 5 | 28 | 152-154 | 86 | 0.81 | 0.94 | 3.85 | 94.40 |
| 6 | 22 | 152-154 | 93 | 0.96 | 0.85 | 4.97 | 93.22 |
| 7 | 22 | 152-154 | 84 | 1.15 | 0.59 | 4.88 | 93.38 |
| 8 | 36 | 152-154 | 73 | 1.12 | 0.43 | 4.60 | 93.85 |
| 9 | 30 | 152-154 | 92 | 1.12 | 0.30 | 4.58 | 94.00 |
| 10 | 33 | 152-154 | 97 | 0.93 | 0.95 | 5.10 | 93.02 |
| 11 | 28 | 152-154 | 101 | 1.08 | 0.78 | 5.12 | 93.02 |

The crude 2-hydrocarbyl-3,3-bis(4-hydroxyaryl)phthalimidine products obtained above were purified by trituration and washing using the same steps as described above in Examples 1 to 3 to obtain purified 2-hydrocarbyl-3,3-bis(4-hydroxyaryl)phthalimidine products. Methanol:water at different ratios as shown in Table 4 were used as the triturating solvents. The results of the purifications are summarized in Table 4.

TABLE 4

| | Triturating solvent (methanol:water; v:v) | AP impurity % | PP impurity % | Total other impurity, % | Purified product purity % |
|---|---|---|---|---|---|
| 4 | 10:1 | 0.8 | 0.0 | 0.8 | 98 |
| 5 | 8:1 | 0.7 | 0.1 | 1.3 | 98 |
| 6 | 7:1 | 0.8 | 0.1 | 1.4 | 97 |
| 7 | 7:1 | 1.0 | 0.20 | 1.6 | 97 |
| 8 | 7:1 | 0.6 | 0.20 | 0.9 | 98 |
| 9 | 7:1 | 0.9 | 0.0 | 1.2 | 98 |
| 10 | 7:1 | 1.0 | 0.2 | 2.1 | 97 |
| 11 | 7:1 | 0.9 | 0.1 | 1.4 | 98 |

As can be seen from the data in Table 4, the purities of the purified 2-hydrocarbyl-3,3-bis(4-hydroxyphenyl)phthalimidine products obtained using phenolphthalein having a purity of 94-95 wt % as starting materials are in the range of 96.77 to 98.41%. The yield loss was 5-7 weight percent.

Examples 12 to 19

Phenolphthalein starting materials (200 grams) having a purity of 97-98 wt % were reacted with aniline. The molar ratio of aniline:phenolphthalein:HCl was 3:1:1. The reactions were quenched with 10 wt % HCl to form a slurry. The slurry was filtered to isolate the precipitate and the precipitate was washed with water. Results are shown in Table 5.

TABLE 5

|    | Time (hours) | Temp (° C.) | Amount of PP (gm) | Out Put (gm) | AP impurity (%) | PP impurity (%) | Total other impurity (%) | Product purity (%) |
|----|-----|---------|-----|-----|------|------|------|-------|
| 12 | 26  | 152-154 | 200 | 208 | 0.37 | 0.26 | 0.70 | 98.67 |
| 13 | 26  | 152-154 | 200 | 206 | 0.30 | 0.41 | 0.74 | 98.55 |
| 14 | 31  | 150-154 | 100 | 109 | 0.42 | 0.72 | 1.99 | 96.87 |
| 15 | 26  | 150-154 | 100 | 115 | 0.62 | 0.71 | 2.05 | 96.63 |
| 16 | 34  | 150-154 | 100 | 108 | 0.34 | 2.12 | 2.19 | 95.35 |
| 17 | 26.5| 150-154 | 100 | 108 | 0.53 | 0.46 | 2.04 | 96.97 |
| 18 | 30  | 150-154 | 100 | 107 | 0.52 | 0.49 | 1.86 | 97.14 |
| 19 | 46  | 150-154 | 150 | 158 | 0.47 | 0.93 | 1.82 | 96.78 |

The precipitates were purified by trituration and washing using the same steps as described above. Methanol:water at different ratios as shown in Table 6 were used as triturating solvents. The results are summarized in Table 6.

TABLE 6

| Ex. # | methanol:water v:v | AP impurity % | PP impurity % | Total other impurity % | Purified product purity % |
|-------|------|-----|-----|-----|------|
| 12 | 6:1 | 0.3 | 0.0 | 0.3 | 99.4 |
| 13 | 6:1 | 0.3 | 0.0 | 0.3 | 99.3 |
| 14 | 6:1 | 0.4 | 0.1 | 0.5 | 99.1 |
| 15 | 7:1 | 0.5 | 0.1 | 0.4 | 99.1 |
| 16 | 7:1 | 0.3 | 0.1 | 0.4 | 99.2 |
| 17 | 8:1 | 0.5 | 0.0 | 0.4 | 99.1 |
| 18 | 8:1 | 0.4 | 0.0 | 0.3 | 99.2 |
| 19 | 8:1 | 0.5 | 0.1 | 0.4 | 99.1 |

As can be seen from the data in Table 6, the purities of the purified 2-hydrocarbyl-3,3-bis(4-hydroxyaryl)phthalimidine products obtained were in the range of 99.05 to 99.36%.

Examples 20 to 25 and Comparative Examples B and C

In Examples 20 to 25 and Comparative Examples B and C, 2-hydrocarbyl-3,3-bis(4-hydroxyphenyl)phthalimidine (PP-PBP) monomers having different purities were used to make polycarbonates by melt polymerization. The properties of the polycarbonates made are summarized in Table 7.

TABLE 7

|    | PPPBP Purity (%) | Mw | Mn | PDI | Tg (° C.) | 5 wt % loss temperature (° C.) | 10 wt % loss temperature (° C.) | 50 wt % loss temperature (° C.) |
|----|-------|-------|-------|-------|--------|--------|--------|--------|
| 20 | 98    | 32067 | 15903 | 2.02  | 204.63 | 417.20 | 446.44 | 495.18 |
| 21 | 99.08 | 32998 | 16264 | 2.03  | 199.03 | 418.19 | 443.93 | 491.74 |
| 22 | 99.68 | 44633 | 19652 | 2.27  | 215.83 | 416.58 | 448.85 | 498.71 |
| 23 | 99.9  | 29362 | 14696 | 2.00  | 197.97 | 421.55 | 451.65 | 496.68 |
| 24 | 98.23 | 29164 | 15178 | 1.92  | 202.88 | 422.68 | 448.42 | 500.1  |
| 25 | 97    | 43469 | 18234 | 2.38  | 203.28 | 429.91 | 454.62 | 498.3  |
| B  | 95    | 32090 | 9281  | 3.458 | 190.98 | 400-454, completely degrades | | |
| C  | 96    | 75236 | 13453 | 5.590 | 197.33 | 412.58 | | |

It can be seen from the data in Table 7 that 2-hydrocarbyl-3,3-bis(4-hydroxyphenyl)phthalimidine monomers having a purity of greater than or equal to 97% can be used to make polymers with desirable properties such as high molecular weight, low polydispersity index (PDI), and high thermal stability. In contrast, polymers obtained from 2-hydrocarbyl-3,3-bis(4-hydroxyaryl)phthalimidine monomers having a purity of less than or equal to 97% (Comparative Examples B and C) have less desirable and unstable properties.

While the disclosure has been described with reference to certain particular embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from essential scope thereof. Therefore, it is intended that the disclosure not be limited to the particular embodiment disclosed as the best mode contemplated for carrying out this invention, but that the disclosure will include all embodiments falling within the scope of the appended claims.

What is claimed is:

1. A method comprising:
reacting a phenolphthalein material and a primary hydrocarbyl amine in the presence of an acid catalyst to form a reaction mixture comprising 2-hydrocarbyl-3,3-bis(4-hydroxyaryl)phthalimidine, wherein the phenolphthalein material comprises greater than or equal to 95 weight percent phenolphthalein, based on the total weight of phenolphthalein material;
quenching the reaction mixture;
treating the quenched reaction mixture to obtain a first solid;
triturating the first solid with a triturating solvent and washing to obtain a second solid, wherein the second solid comprises greater than or equal to 97 weight percent 2-hydrocarbyl-3,3-bis(4-hydroxyaryl)phthalimidine, based on the total weight of the second solid; and
wherein the 2-hydrocarbyl-3,3-bis(4-hydroxyaryl)phthalimidine has a formula of:

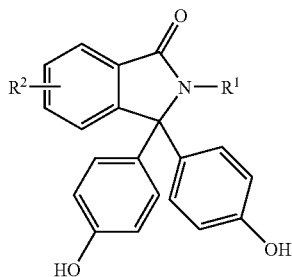

wherein $R^1$ is selected from the group consisting of a hydrogen, and a hydrocarbyl group, and $R^2$ is selected from the group consisting of a hydrogen, a hydrocarbyl group, and a halogen.

2. The method of claim 1 wherein quenching is performed with an acid and forms a slurry comprising a precipitate and treating the quenched reaction mixture comprises:
filtering the slurry to isolate the precipitate; and
washing the precipitate with water to obtain a washed precipitate, wherein the water has a temperature of 25 to 90° C. to obtain the first solid.

3. The method of claim 2, wherein the acid used in quenching is aqueous hydrochloric acid.

4. The method of claim 1, wherein the quenching is performed with aqueous base and forms a biphasic system and treating the quenched reaction mixture comprises:
adding an organic solvent to the biphasic system;
removing the basic layer of the biphasic system after adding the organic solvent;
acidifying the basic layer and forming a first solid; and
isolating the first solid.

5. The method of claim 4, wherein the basic layer is treated with an adsorbent prior to acidification.

6. The method of claim 1, wherein the phenolphthalein material comprises greater than or equal to 97 weight percent phenolphthalein, based on the total weight of the phenolphthalein material.

7. The method of claim 1, wherein the phenolphthalein material and the primary hydrocarbyl amine are reacted at a temperature of 140° C. to 180° C. for 8 to 50 hours.

8. The method of claim 1, wherein the acid catalyst is selected from the group consisting of hydrochloric acid, sulfuric acid, nitric acid, phosphoric acid, boric acid, organic sulfonic acids, stannic chloride, aluminum trichloride, zinc dichloride; sulfated zirconia, and combinations of two or more of the foregoing acid catalysts.

9. The method of claim 1, wherein the catalyst is hydrochloric acid.

10. The method of claim 1, wherein the triturating solvent is a methanol:water mixture.

11. The method of claim 1, wherein the primary hydrocarbyl amine is aniline.

12. The method of claim 11, wherein the second solid comprises 2-phenyl-3,3-bis(4-hydroxphenyl)phthalimidine.

13. The method of claim 1, wherein the second solid comprises greater than or equal to 99 weight percent 2-hydrocarbyl-3,3-bis(4-hydroxyaryl)phthalimidine, based on the total weight of the second solid.

14. The method of claim 1, wherein the second solid is polymerizable.

15. The method of claim 1, wherein the second solid comprises less than or equal to 50 parts per million by weight of residual solvent based on the total weight of the second solid.

16. The method of claim 1, wherein the second solid comprises less than or equal to 1000 parts per million by weight of phenolphthalein based on the total weight of the second solid.

17. The method of claim 16, wherein the second solid comprises less than or equal to 500 parts per million by weight of phenolphthalein based on the total weight of the second solid.

18. A method of making a polycarbonate comprising:
reacting a phenolphthalein material and a primary hydrocarbyl amine in the presence of an acid catalyst to form a reaction mixture comprising 2-hydrocarbyl-3,3-bis(4-hydroxyaryl)phthalimidine, wherein the phenolphthalein material comprises greater than or equal to 95 weight percent phenolphthalein, based on the total weight of phenolphthalein material;
quenching the reaction mixture;
treating the quenched mixture to obtain a first solid;
triturating the first solid with a triturating solvent and washing the solid after trituration to obtain a second solid wherein the second solid comprises greater than or equal to 97 weight percent 2-hydrocarbyl-3,3-bis(4-hydroxyaryl)phthalimidine, based on the total weight of the second solid; and wherein the 2-hydrocarbyl-3,3-bis(4-hydroxyaryl)phthalimidine has a formula of:

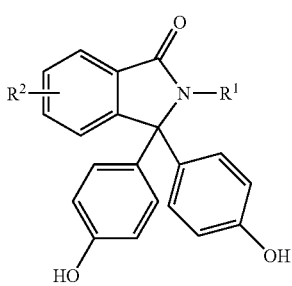

wherein $R^1$ is selected from the group consisting of a hydrogen, and a hydrocarbyl group, and $R^2$ is selected from the group consisting of a hydrogen, a hydrocarbyl group, and a halogen; and polymerizing the third solid to form a polycarbonate.

19. The method of claim 18, wherein polymerizing the second solid comprises interfacial polymerization or melt polymerization.

20. The method of claim 18, wherein quenching is performed with an acid and forms a slurry comprising a precipitate and treating the quenched reaction mixture comprises:

filtering the slurry to isolate the precipitate; and washing the precipitate with water to obtain a washed precipitate, wherein the water has a temperature of 25 to 90° C. to obtain the first solid.

21. The method of claim 20, wherein the acid used in quenching is aqueous hydrochloric acid.

22. The method of claim 18, wherein the quenching is performed with aqueous base and forms a biphasic system and treating the quenched reaction mixture comprises:

adding an organic solvent to the biphasic system;

removing the basic layer of the biphasic system after adding the organic solvent;

acidifying the basic layer and forming a first solid; and isolating the first solid.

* * * * *